(12) United States Patent
Hoffman

(10) Patent No.: US 7,431,190 B2
(45) Date of Patent: Oct. 7, 2008

(54) LINEAR STAPLER WITH IMPROVED FIRING MECHANISM

(75) Inventor: Douglas B. Hoffman, Harrison, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 43 days.

(21) Appl. No.: 11/366,639

(22) Filed: Mar. 1, 2006

(65) Prior Publication Data

US 2007/0215670 A1    Sep. 20, 2007

(51) Int. Cl.
*A61B 17/04* (2006.01)
*A61B 17/10* (2006.01)

(52) U.S. Cl. .................... 227/178.1; 227/19; 227/181.1
(58) Field of Classification Search .................... 227/19, 227/178.1, 180.1, 181.1
See application file for complete search history.

(56) References Cited

U.S. PATENT DOCUMENTS

| | | | |
|---|---|---|---|
| 3,692,224 A | | 9/1972 | Astafiev et al. |
| 4,522,327 A | * | 6/1985 | Korthoff et al. ................ 227/19 |
| 4,606,345 A | * | 8/1986 | Dorband et al. ........... 227/181.1 |
| 4,607,636 A | * | 8/1986 | Kula et al. ................ 227/181.1 |
| 4,684,051 A | * | 8/1987 | Akopov et al. ................. 227/19 |
| 4,741,336 A | * | 5/1988 | Failla et al. ............... 227/181.1 |
| 4,869,414 A | * | 9/1989 | Green et al. .................... 227/19 |
| 5,137,198 A | * | 8/1992 | Nobis et al. ............... 227/175.3 |
| 5,240,163 A | * | 8/1993 | Stein et al. ................ 227/175.3 |
| 5,413,267 A | * | 5/1995 | Solyntjes et al. .......... 227/175.4 |
| 5,458,279 A | * | 10/1995 | Plyley ....................... 227/176.1 |
| 5,470,009 A | * | 11/1995 | Rodak ....................... 227/176.1 |
| 5,626,587 A | * | 5/1997 | Bishop et al. ................ 606/143 |
| 5,704,534 A | * | 1/1998 | Huitema et al. ........... 227/175.1 |
| 5,706,998 A | | 1/1998 | Plyley et al. |
| 6,119,913 A | * | 9/2000 | Adams et al. ............. 227/176.1 |
| 6,302,311 B1 | * | 10/2001 | Adams et al. ............. 227/176.1 |
| 6,695,198 B2 | * | 2/2004 | Adams et al. ............. 227/175.1 |
| 6,827,246 B2 | * | 12/2004 | Sullivan et al. ........... 227/180.1 |

* cited by examiner

*Primary Examiner*—Brian Nash

(57) ABSTRACT

A surgical stapler comprising including an elongated handle portion having a longitudinal axis extending between a distal end and a proximal end. The stapler includes an end effector disposed at the distal end of the handle having a staple cartridge housing, and an anvil. The end effector has an open position wherein the staple cartridge and the anvil are spaced apart, and a closed position wherein the staple cartridge and anvil are closely adjacent to each other. The stapler also includes an elongated trigger. The distal end of the trigger being pivotably attached to the handle between the handle's distal and proximal end. The trigger has an open position wherein the proximal end of the trigger is spaced apart from the handle, and a closed position wherein the proximal end of the trigger is closely adjacent the handle. The trigger is linked to the end effector such that moving the trigger from its open to its closed position moves the end effector from its open to its closed position. The stapler also includes an actuator for ejecting the plurality of staples from the cartridge towards the anvil. The actuator includes a rotatable knob mounted onto the distal end of the handle, such that progressive rotation of the knob in a predetermined direction progressively ejects the staples.

9 Claims, 9 Drawing Sheets

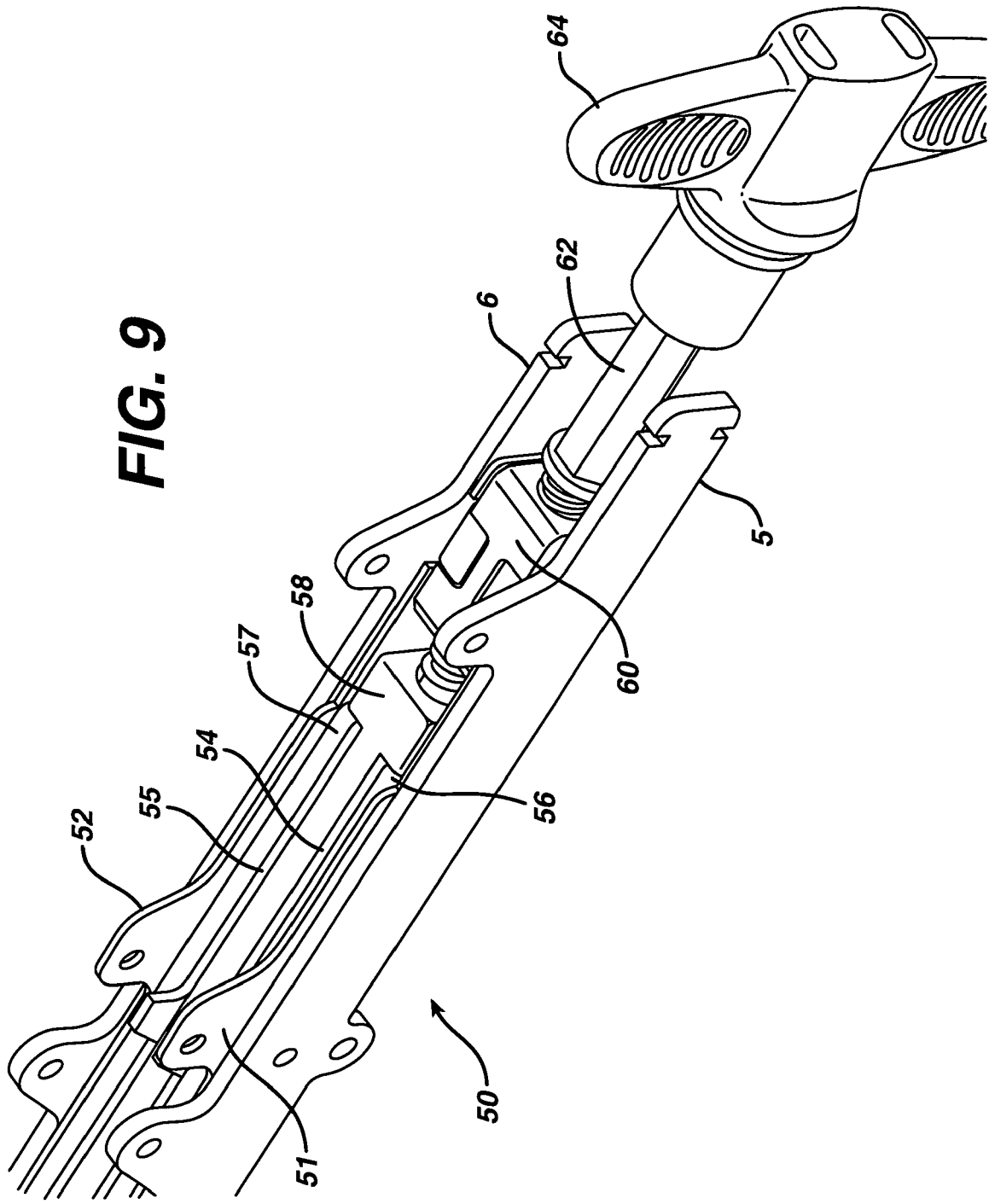

LINEAR STAPLER WITH IMPROVED FIRING MECHANISM

FIELD OF THE INVENTION

The present invention has application in conventional open surgical instrumentation as well application in robotic-assisted surgery. The present invention has even further relation to linear staples and staplers.

BACKGROUND OF THE INVENTION

Surgical staplers are frequently used in surgical procedures for suturing body tissues such as, for example, intestinal and gastric walls. Such devices typically include a staple holder, or cartridge, which is disposed on one side of the tissue to be fastened and an anvil assembly on the other side of the tissue. During the surgical procedure, the staples are driven from the cartridge by some type of actuator so that the ends of the staples pass through the tissue and then are bent inwardly by the anvil so as to produce an array of finished fasteners in the tissue. During the typical suturing process, pusher members associated with the cartridge are controllably advanced by the operating mechanism of the instrument in a manner to urge the staples out of the cartridge, through the tissue and forceably against the anvil.

One such frequently used type of surgical stapler is the open linear stapler, which is a device that enables the surgeon to simultaneously place one or more rows of surgical staples in body tissue or organs. By way of example, a typical procedure is a pneumectomy, which is a removal of a portion of the patient's lungs. The linear stapler can be used several times during this procedure, including for the occlusion of the pulmonary artery prior to its resection. For this later use, the surgeon first clamps the jaws of the stapler across the artery then forms the staple and before reopening the stapler jaws, cuts the artery with a scalpel using the edge of the staple jaws as a guide.

An example of an open linear stapler is disclosed in U.S. Pat. No. 5,706,998 issued to Plyley et al. A surgical stapler is described having a supporting frame including a stationary jaw having an anvil, a movable jaw, a replaceable staple cartridge carried by the movable jaw, a mechanism for approximating the cartridge relative to the anvil, and a mechanism for firing the device so as to crimp the staples against the anvil in a manner to enable the surgeon to substantially simultaneously place one or more rows of surgical staples in organs or tissues. The device includes interrelated, cooperating first and second locking mechanisms for positively preventing refiring if the staple cartridge is spent and for providing a tactile sensation to the surgeon to indicate that a spent staple cartridge is present within the instrument. One of the drawbacks to this design is the large amount of force required for the surgeon to fire the staples using the firing mechanism. Having an open linear stapler with a large amount of force required for the surgeon to fire the staples limits the number of surgeons that can actually use the device because of the strength required to actuate the firing mechanism. Another drawback of this design is the fact that no cutting means, or knife, is available to use after the staples have been fired.

Another example of an open linear stapler is disclosed in U.S. Pat. No. 3,692,224 issued to Astafiev et al. A surgical stapling apparatus is described including a support housing having an open longitudinal cavity wherein slidable rods of the staple housing and pusher are accommodated. The staple housing has a head provided with a socket in which a magazine with staples in entirely inserted. The staple housing and the pusher are provided with screw drives to axially shift them relative to the support housing. The apparatus also includes a limit strip capable of retaining the magazine when it is completely pushed into the socket and holding the tissue being sutured. The limit strip interacts with the nut of the drive of the staple housing whereby the drive of the pusher is blocked with the drive of the staple housing in such a manner that a predetermined sequence of actions is provided during the operation of the apparatus. In accordance with this sequence, the staple housing can move only after the magazine is completely pushed into the socket of the staple housing and the pusher can displace only after the staple housing has defined for a maximal suturing gap between the working surface of the magazine and the die. One of the drawbacks of this design is the inability to grasp the tissue and secure it prior to firing the staples. Without being able to secure the tissue, if a surgeon slips firing the device, he or she may misplace the staples from their intended position. Another drawback of this design is the fact that no cutting means, or knife, is available to use after the staples have been fired.

The prior art open linear staplers all exhibit one or more drawbacks that have thus far limited their usefulness to the surgeon using these open linear staplers. What is needed therefore is an open linear stapler that has a low actuation force required to fire the staples and an integrated knife, which also cuts with this low actuation force.

SUMMARY OF THE INVENTION

The present invention provides surgical stapler comprising including an elongated handle portion having a longitudinal axis extending between a distal end and a proximal end. The stapler includes an end effector disposed at the distal end of the handle having a staple cartridge housing, and an anvil. The end effector has an open position wherein the staple cartridge and the anvil are spaced apart, and a closed position wherein the staple cartridge and anvil are closely adjacent to each other. The stapler also includes an elongated trigger. The distal end of the trigger being pivotably attached to the handle between the handle's distal and proximal end. The trigger has an open position wherein the proximal end of the trigger is spaced apart from the handle, and a closed position wherein the proximal end of the trigger is closely adjacent the handle. The trigger is linked to the end effector such that moving the trigger from its open to its closed position moves the end effector from its open to its closed position. The stapler also includes an actuator for ejecting the plurality of staples from the cartridge towards the anvil. The actuator includes a rotatable knob mounted onto the distal end of the handle, such that progressive rotation of the knob in a predetermined direction progressively ejects the staples.

BRIEF DESCRIPTION OF THE FIGURES

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 9 illustrates a side view of internal components of the linear stapler of the present invention showing the safety mechanism through which the trigger cannot be opened while firing.

DETAILED DESCRIPTION OF THE INVENTION

As used herein, the term "proximal" refers to a location on the linear stapler closest to the clinician using the device and thus furthest from the patient on which the device is used. Conversely, the term "distal" refers to a location farthest from the clinician and closest to the patient.

Figure 1:
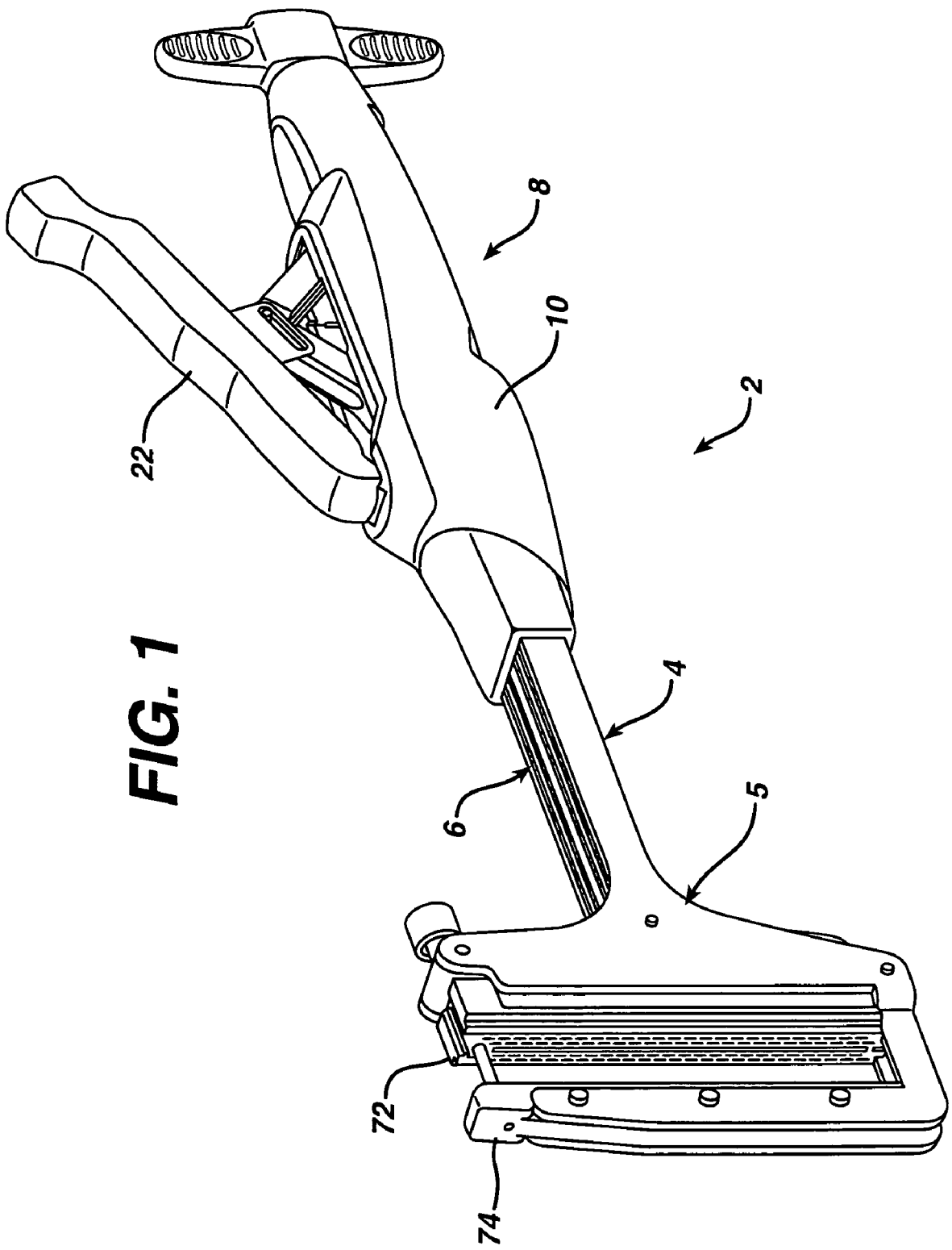
FIG. 1 illustrates an isometric view of the linear stapler of the present invention in its open position.

As illustrated in FIG. 1, linear stapler 2 comprises of frame assembly 4, closure assembly 20, firing assembly 50, and a U-shaped end effector 70. Frame assembly 4 includes first hook 5 and second hook 6. First hook 5 and second hook 6, which can be made of, but is not limited to, stainless steel, play an integral role in connecting end effector 60 to frame assembly 4, which will be described in more detail later. Frame assembly 4 further includes handle outer shrouding 8. Handle outer shrouding 8, which can be used to grip and maneuver linear stapler 2, includes left handle shrouding 10 and right handle shrouding 11 (not shown but opposite of left handle shrouding 10). Right handle shrouding 11 and left handle shrouding 10 are preferably made of a polymer such as, for example, polycarbonate. Right handle shrouding 11 can be coupled to left handle shrouding 10 by gluing or any other suitable attachment means suitable to those skilled in the art to form handle outer shrouding 8 of frame assembly 4.

Figure 2:
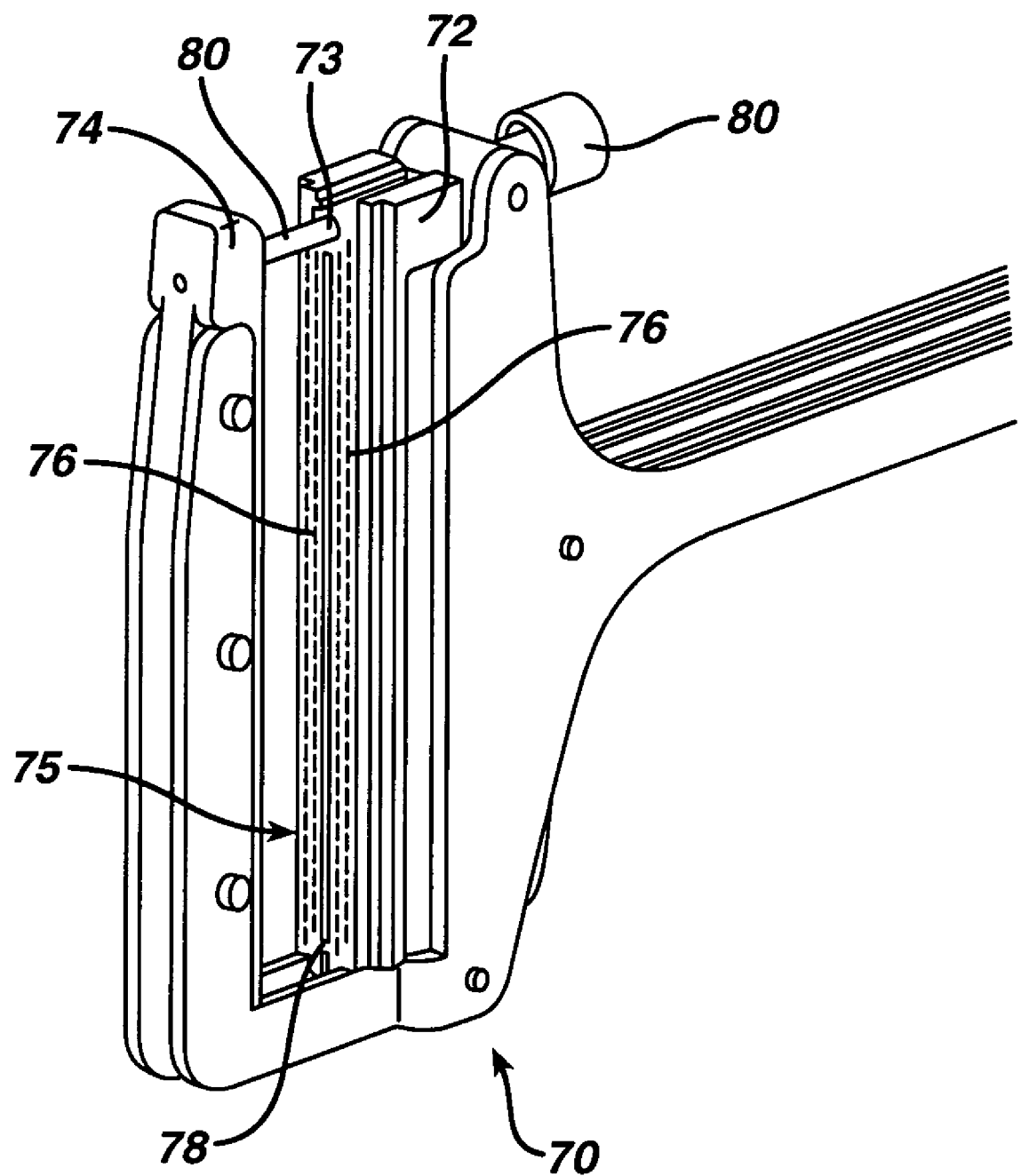
FIG. 2 illustrates an isometric view of the end effector of the linear stapler of the present invention.
Figure 3:
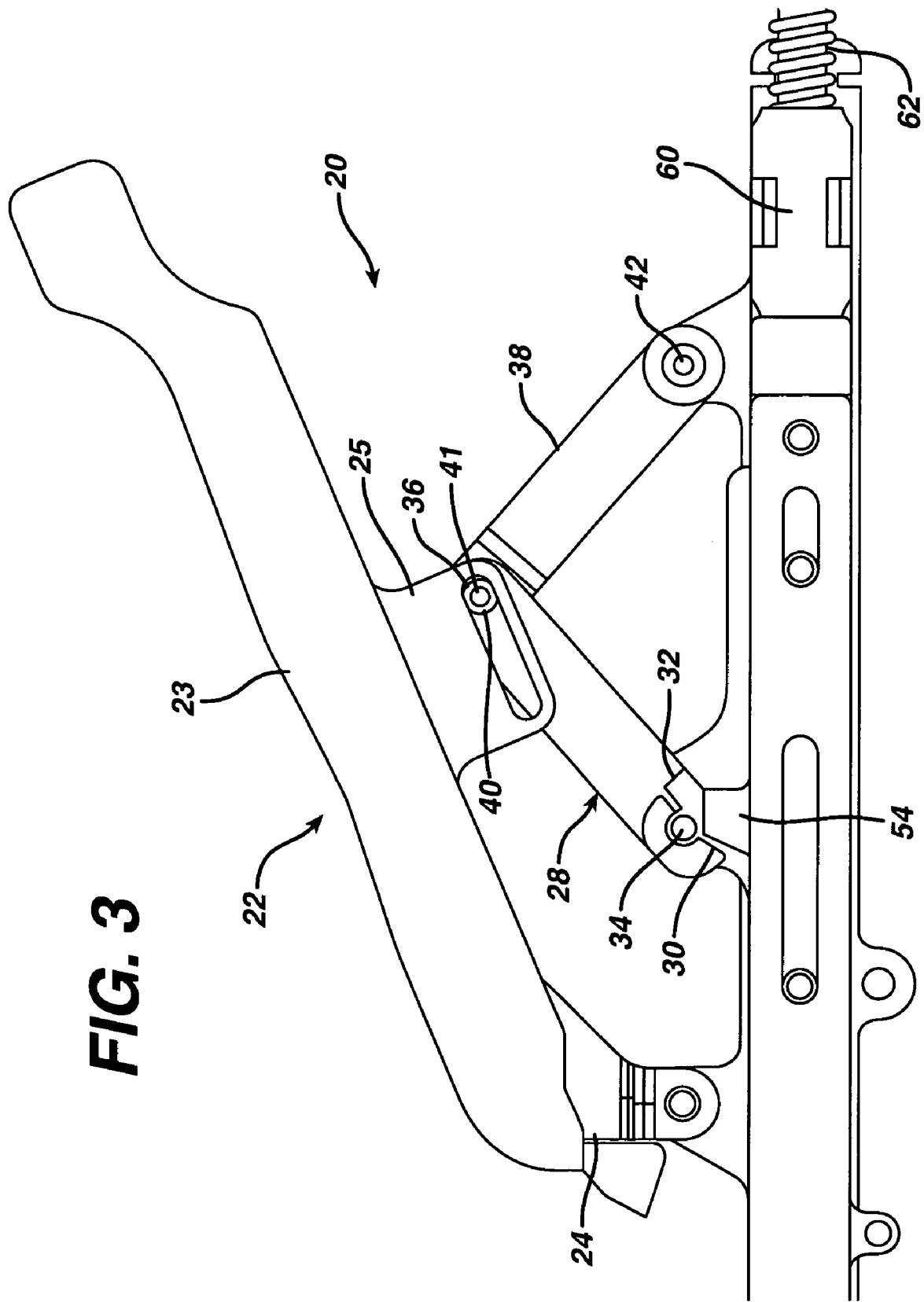
FIG. 3 illustrates an isometric view of the linear stapler of the present invention in its open and pre-stapled position with the outer handle shrouding removed to expose inner components.
Figure 4:
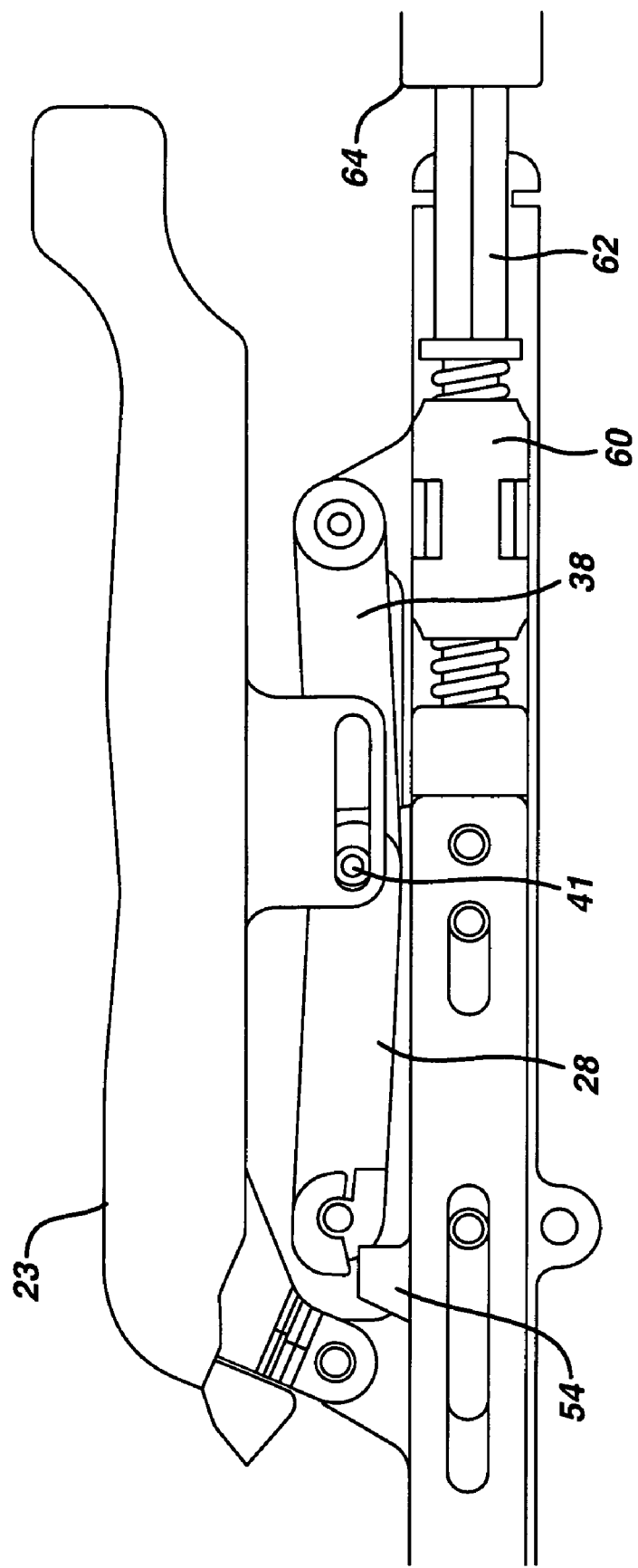
FIG. 4 illustrates an isometric view of the linear stapler of the present invention in its closed and pre-stapled position with the outer handle shrouding of the invention is removed to expose inner components.

Referring to FIG. 2, end effector 70, which is located at the proximal end of linear stapler 2, includes cartridge 72 and anvil 74. The cartridge 72 has a tissue contacting surface 75 which displays a plurality of staple- containing slots 76 in vertical rows. Cartridge 72 further includes an opening 73 therethrough located at its top end and an integrated knife 78 therein. Integrated knife 78 can be actuated by the firing assembly 50, which will be described in more detail later, to cut the tissue between the rows of staples formed therearound. Staples (not shown) are fired from the cartridge 72 against the staple-forming surface of the anvil 74 (not shown), which faces the tissue-contacting surface 75 of the cartridge 72. End effector 70 further includes end effector pin 80, which is preferably made of, but is not limited to, stainless steel. End effector pin 80 can be slid through opening 73 of cartridge 72 and screwed into a circular screw slot located at the top end of anvil 74 (not shown) to help secure the frame assembly 4, the cartridge 72 and the anvil 74 and will be described in more detail later.

Figure 5:
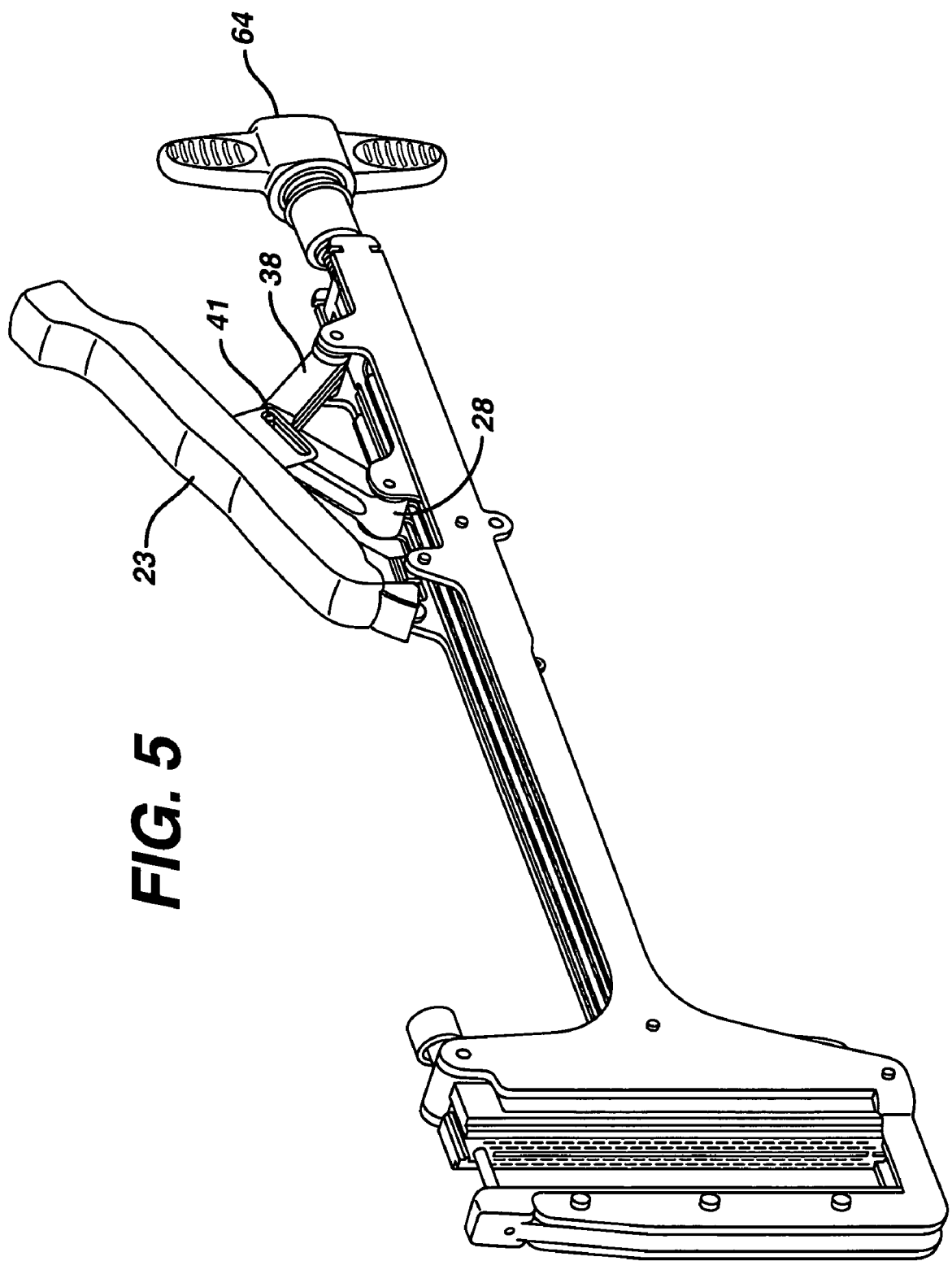
FIG. 5 illustrates a close-up isometric view of proximal internal components of the linear stapler of the present invention showing the linear stapler in its open and post-stapled position.
Figure 6:
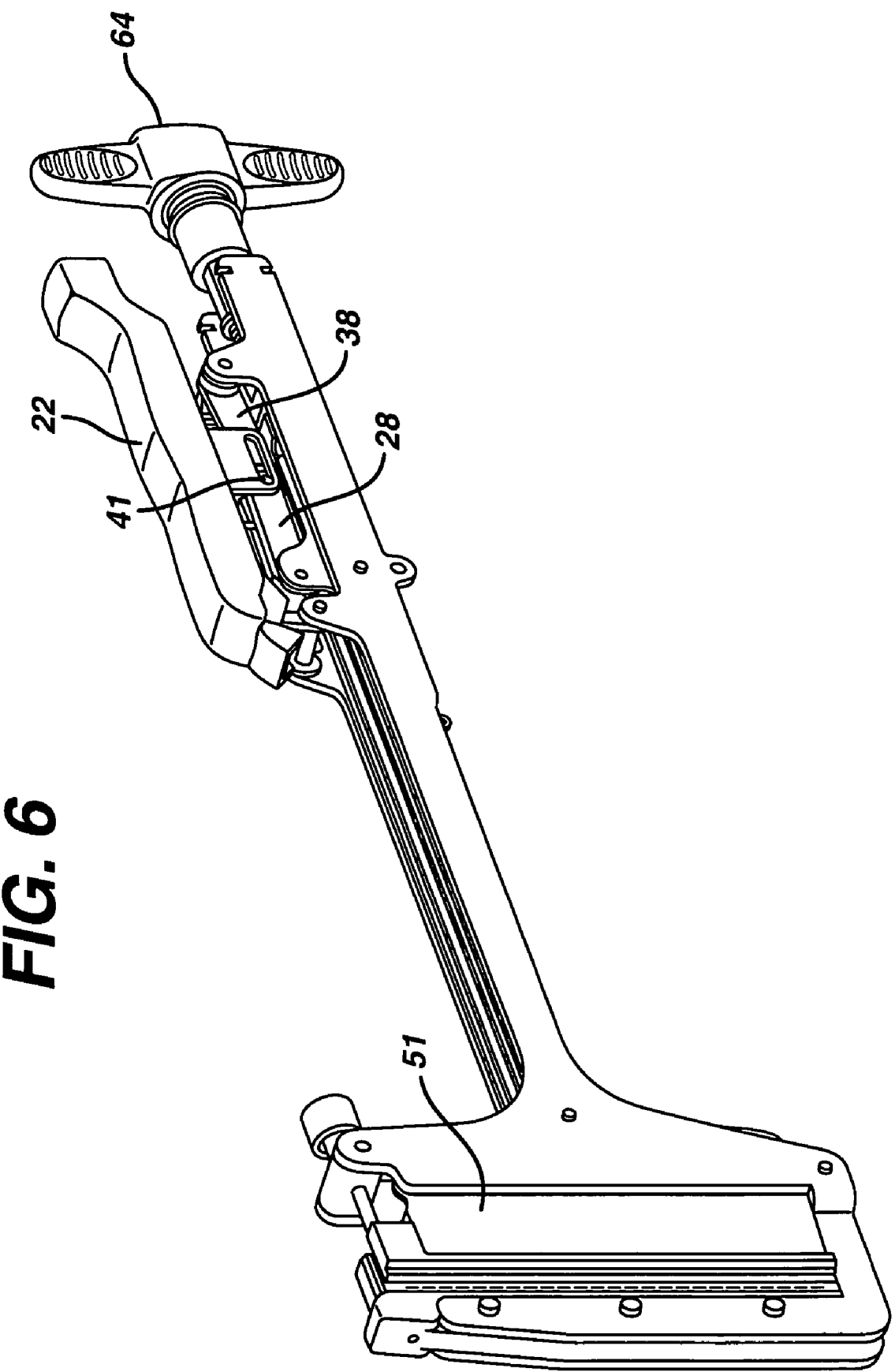
FIG. 6 illustrates a close-up isometric view of proximal internal components of the linear stapler of the present invention showing the linear stapler in its closed and post-stapled position.

As illustrated in FIG. 1, linear stapler 2 comprises of frame assembly 4, closure assembly 20 (FIG. 8), firing assembly 50 (FIG. 5), and a U-shaped end effector 70. Frame assembly 4 includes first hook 5 and second hook 6. First hook 5 and second hook 6, which can be made of, but is not limited to, stainless steel, play an integral role in connecting end effector 70 to frame assembly 4, which will be described in more detail later. Frame assembly 4 further includes handle outer shrouding 8. Handle outer shrouding 8, which can be used to grip and maneuver linear stapler 2, includes left handle shrouding 10 and right handle shrouding 11. Right handle shrouding 11 and left handle shrouding 10 are preferably made of a polymer such as, for example, polycarbonate. Right handle shrouding 11 can be coupled to left handle shrouding 10 by gluing or any other suitable attachment means suitable to those skilled in the art to form handle outer shrouding 8 of frame assembly 4.

Referring to FIG. 2, end effector 70, which is located at the proximal end of linear stapler 2 (FIG. 1), includes cartridge 72 and anvil 74. The cartridge 72 has a tissue contacting surface 75 which displays a plurality of staple-containing slots 76 in vertical rows. Cartridge 72 further includes an opening 73 therethrough located at its top end and an integrated knife 78 therein. Integrated knife 78 can be actuated by the firing assembly 50 (FIG. 5), which will be described in more detail later, to cut the tissue between the rows of staples formed therearound. Staples (not shown) are fired from the cartridge 72 against the staple-forming surface of the anvil 74 (not shown), which faces the tissue-contacting surface 75 of the cartridge 72. End effector 70 further includes end effector pin 80, which is preferably made of, but is not limited to, stainless steel. End effector pin 80 can be slid through opening 73 of cartridge 72 and screwed into a circular screw slot located at the top end of anvil 74 (not shown) to help secure the frame assembly 4, the cartridge 72 and the anvil 74 and will be described in more detail later.

Figure 7:
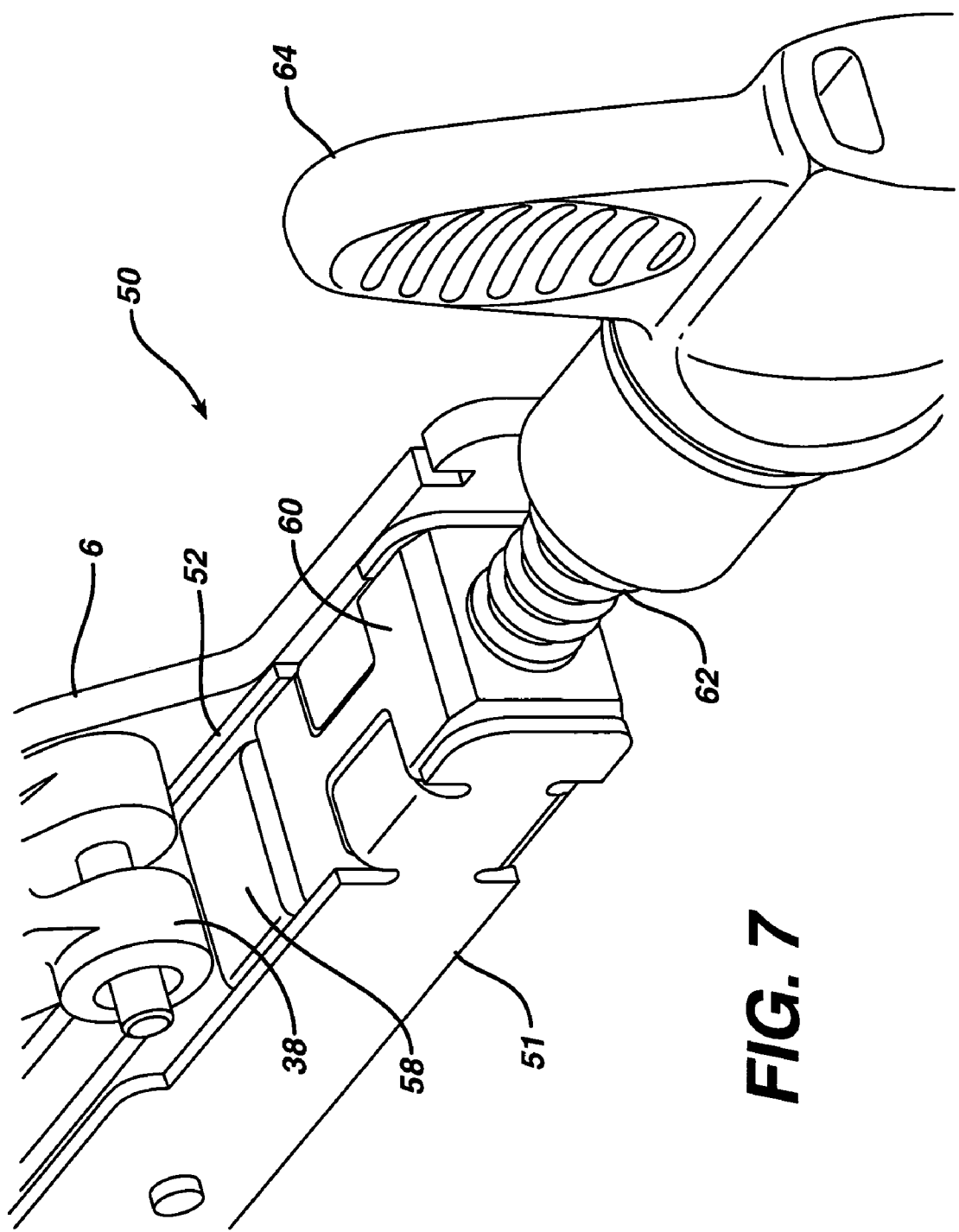
FIG. 7 illustrates an isometric view of internal components of the linear stapler of the present invention showing the linear stapler in its closed and stapled position.
Figure 8:
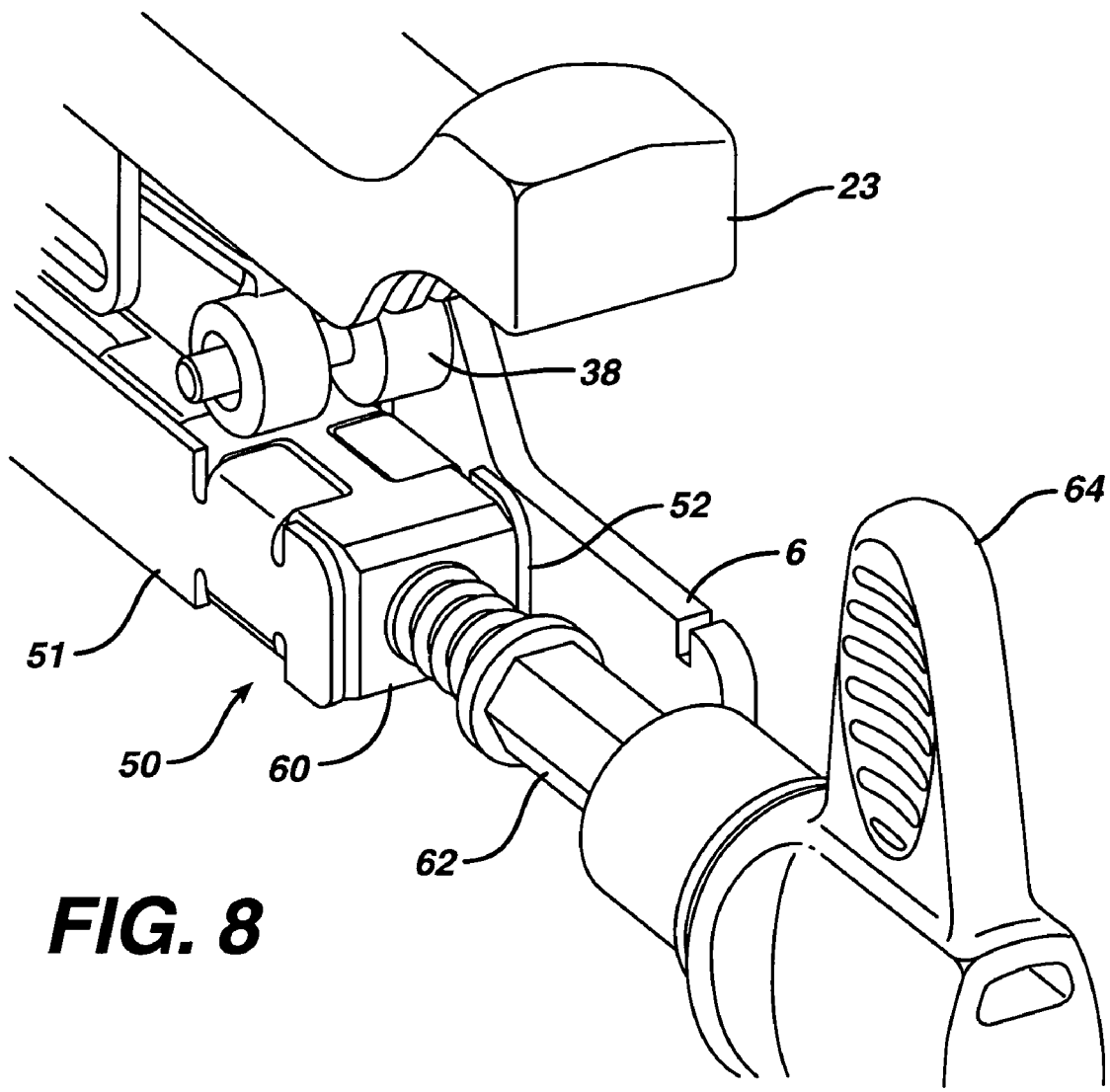
FIG. 8 illustrates a side view of internal components of the linear stapler of the present invention showing the safety mechanism through which the firing bars cannot be advanced until the trigger is closed.

As illustrated in FIGS. 8-9, closure assembly 20 includes trigger 22, first linkage system 28, second linkage system 38, closure assembly pin 41, first closure plate 51 (FIG. 7), and second closure plate 52 (FIG. 7). Trigger 22 includes a trigger shrouding 23, a first frame wing 24, and a second frame wing 26 (not shown but opposite first frame wing 24). Trigger shrouding 23, which can be made of, but is not limited to a polymer such as, for example, polycarbonate, has a first sidewall and second sidewall. First frame wing 24, which can be made of, but is not limited to, stainless steel, extends downward from the distal end of first side of trigger shrouding 23. Similarly, second frame wing 26, which can be made of, but is not limited to, stainless steel, extends downward from the distal end of second side of trigger shrouding 23. Trigger 22 further includes first linkage plate 25 and second linkage plate 27 (not shown but opposite first linkage plate 25). First linkage plate 25, which can be made of but is not limited stainless steel, extends downward from the first sidewall of trigger shrouding 23 between its proximal and distal ends. First linkage plate 25 has a slot therein which plays an integral role in connecting first linkage system 28 and second linkage system 38 to trigger shrouding 23 and will be described in more detail later. Second linkage plate 27, which can be made of but is not limited stainless steel, extends downward from the second sidewall of trigger shrouding 23 between its proximal and distal ends. Second linkage plate 27 has a slot therein which plays an integral role in connecting first linkage system 28 and second linkage system 38 to trigger shrouding 23 and will be described in more detail later. First linkage system 28, which can be made of, but is not limited to, a polymer such as, for example, ultem, has a proximal end and a distal end. At the distal end of first linkage system 28 is lock surface 30, and first linkage system pin 34. At the proximal end of first linkage system 28 is first closure assembly pin opening 36. Second linkage system 38, which can be made of, but is not limited to, a polymer such as, for example, ultem, has a proximal end and a distal end. At the distal end of second linkage system 38 is second closure assembly pin opening 40. At the proximal end of second linkage system 38 is second linkage system pin 42. Second linkage system pin 42 plays an integral role in connecting frame assembly 4 to trigger 22 and will be described in more detail later. First linkage system 28 is assembled to second linkage system 38 such that first closure assembly pin opening 36 is aligned with second closure assembly pin opening 40 thereby allowing closure assembly pin 41 to be inserted therethrough. Trigger 22 is then assembled to first linkage system 28 and second linkage system 38 such that closure assembly pin 41 resides in both slots of first linkage plate 25 and second linkage plate 27.

As shown in FIGS. 3-7, firing mechanism 50 includes first closure plate 51, second closure plate 52, first firing bar 54, second firing bar 55, first spacer 56, second spacer 57, knife bar 58, screw block 60, drive screw 62, and stapling knob 64. First closure plate 51 and second closure plate 52, which can be made of, but is not limited to, stainless steel, play an integral role in both closure mechanism 20 and firing mechanism 40 and will be described in more detail later. Attached to the proximal end of first closure plate 51 and second closure plate 52 is screw block 60. Screw block 60, which can be made of, but is not limited to, a polymer such as, for example, ultem, includes drive screw 62 passing therethrough. Drive screw 62, which has a proximal and distal end, can be made of, but is not limited, to a polymer such as, for example, ultem. Attached to the proximal end of drive screw 62, via a slip fit or any other suitable attachment means known to those skilled in the art, is stabling knob 64. Stapling knob 64, which can be made of, but is not limited to, a polymer such as, for example, polycarbonate, can be used by the surgeon to fire staples from linear stapler 2 at a much smaller force to fire than conventional stapling mechanisms. The distal end of drive screw 62 is attached to the proximal end of knife bar 58 via a rotatable coupling or other known art. Knife bar 58, which has proximal and distal end, can be made of, but is not limited to, a polymer such as, for example, ultem. The distal end of knife bar 58 is attached integrated knife 78 and will be described in more detail later. Knife bar 58 further includes two side walls. Attached to one side wall of knife bar 58 is first firing bar 54, which can be made of, but is not limited to stainless steel. Attached to the opposite side of knife bar 58 is second firing bar 55, which can be made of, but is not limited to, stainless steel. Attached to the outside of first firing bar 54 is first spacer 56. Similarly, attached to the outside of second firing bar 55 is second spacer 57. First spacer 56, which can be made of, but is not limited to, a polymer such as, for example, polycarbonate, has an outside wall. Second spacer 57, which can be made of, but is not limited to, a polymer such as, fore example, polycarbonate, has an outside wall. The outside wall of first spacer 56 slidably situated adjacent to first closure plate 51. Similarly, the outside wall of second spacer 57 slidably situated adjacent to second closure plate 52.

Referring now to FIGS. 3-7, firing assembly 50 is assembled to frame assembly 4 as follows;
the outside of first closure plate 51 is slidably situated adjacent to the inside of first hook 5; and
the outside of second closure plate 52 is slidably situated adjacent to the inside of second hook 6.

Now closure assembly 20 is assembled to frame assembly 4 (FIG. 4) and firing assembly 50 as follows;
first linkage system pin 34 of first linkage system 28 is attached to the opening of wing of first closure plate 51 of firing assembly 50 and the opening of wing of second closure plate 52 of firing assembly 50 respectively; and
second linkage system pin 42 of second linkage system 38 is attached to the opening of wing of first hook 5 of frame assembly 4 (FIG. 4) and the opening of wing of second hook 6 of frame assembly 4 (FIG. 4) respectively.

Finally, frame assembly 4 (FIG. 4) including closure assembly 20 and firing assembly 50 is assembled to end effector 70 as follows;
the distal end of knife bar 58 is attached to the proximal end of integrated knife 78 (FIG. 2) in cartridge 72 (FIG. 2);
the distal end of first firing bar 54 is adjacent to the proximal end of cartridge 72 (FIG. 2) such that it pushes one side of staples out into anvil 74 (FIG. 2) when actuated;
the distal end of second firing bar 55 is adjacent to the proximal end of cartridge 72 (FIG. 2) such that it pushes one side of staples out into anvil 74 (FIG. 2) when actuated;
the distal end of first closure plate 51 is attached to the side of cartridge 72 (FIG. 2) and the distal end of second closure plate 52 is attached to the opposite side of cartridge 72 (FIG. 2) such that when closure mechanism 20 is closed by actuating trigger 22 first closure plate 51 and second closure plate 52 move distally moving cartridge 72 (FIG. 2) distally as well; and
stationary slot pin 67 connects first hook to second hook such that stationary slot pin 67 extends through the slots of the closure plates, spacer plates and the firing bar.

In an actual surgical procedure utilizing the device of the present invention, after gaining access to the surgical site through, the surgeon inserts linear stapler 2 through the access way to the surgical site such that the tissue to be stapled is placed between the staple cartridge 72 and anvil 74 of the end effector 70. As the closure trigger 22 is actuated and the linkage system is closed, first linkage system 28 is moved forward thereby moving the closure plates 51 & 52 forward compressing the target tissue between the anvil 74 and cartridge 72. As the closure plates 51 & 52 are moved forward, the stapling mechanism is moved forward within the frame of the device. At this point the staple knob 64 at the proximal end of the device is rotated. As the stapling knob 64 is rotated the drive screw 62 is rotated and translates distally through the screw block 60. The distal end of the drive screw 62 pushes the knife bar 58 forward thereby pushing the firing bars 54 & 55 forward and forming the staples as well as pushing the knife forward and dividing the tissue at the midline of the staples. The staples and knife are timed as to allow for the majority of the staple forming operation to occur before the knife divides the tissue.

Lastly, it is preferred that device disclosed above be sterilized. This can be done by any number of ways known to those skilled in the art including beta or gamma radiation, ethylene oxide, steam.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, as would be apparent to those skilled in the art, the disclosures herein have equal application in robotic-assisted surgery. In addition, it should be understood that every structure described above has a function and such structure can be referred to as a means for performing that function. Accordingly, it is intended that the invention be limited only by the spirit and scope of the appended claims.

What is claimed:

1. A surgical stapler comprising:
   a. an elongated handle portion having a longitudinal axis extending between a distal end and a proximal end;
   b. an end effector disposed at said distal end of said handle, said end effector comprising a staple cartridge housing a plurality of staples, and an anvil, said end effector having an open position wherein said staple cartridge and said anvil are spaced apart, and a closed position wherein said staple cartridge and anvil are closely adjacent to each other;
   c. an elongated trigger having a distal end and a proximal end, said distal end of said trigger being pivotably attached to said handle between said handle's distal and proximal end, said trigger having an open position wherein said proximal end of said trigger is spaced apart from said handle, and a closed position wherein said proximal end of said trigger is closely adjacent said handle, said trigger being linked to said end effector such that moving said trigger from its open to its closed position moves said end effector from its open to its closed position; and
   d. an actuator for ejecting all of said plurality of staples simultaneously from said cartridge towards said anvil in a direction substantially parallel to said longitudinal axis of said handle, said actuator comprising a rotatable knob mounted onto said distal end of said handle, such that progressive rotation of said knob in a predetermined direction progressively ejects said staples.

2. The surgical stapler of claim 1 wherein said cartridge contains a plurality of rows of staples.

3. The surgical stapler of claim 1 wherein said end effector comprises a U shaped member.

4. The surgical stapler of claim 3 wherein said end effector further comprises a slidable pin at a top of said U-shaped member.

5. A surgical stapler comprising:
   a. an elongated handle portion having a longitudinal axis extending between a distal end and a proximal end;
   b. an end effector disposed at said distal end of said handle, said end effector comprising a staple cartridge housing a plurality of staples and a knife, and an anvil, said end effector having an open position wherein said staple cartridge and said anvil are spaced apart, and a closed position wherein said staple cartridge and anvil are closely adjacent to each other;
   c. an elongated trigger having a distal end and a proximal end, said distal end of said trigger being pivotably attached to said handle between said handle's distal arid proximal end, said trigger having an open position wherein said proximal end of said trigger is spaced apart from said handle, and a closed position wherein said proximal end of said trigger is closely adjacent said handle, said trigger being linked to said end effector such that moving said trigger from its open to its closed position moves said end effector from its open to its closed position; and
   d. an actuator for ejecting all of said plurality of staples simultaneously from said cartridge towards said anvil in a direction substantially parallel to said longitudinal axis of said handle, said actuator comprising a rotatable knob mounted onto said distal end of said handle, such that progressive rotation of said knob in a predetermined direction progressively ejects said staples.

6. The surgical stapler of claim 5 wherein said cartridge contains a plurality of rows of staples.

7. The surgical stapler of claim 6 wherein said knife is disposed between said lines of staples.

8. The surgical stapler of claim 5 wherein said end effector comprises a U shaped member.

9. The surgical stapler of claim 8 wherein said end effector further comprises a slidable pin at a top of said U-shaped member.

* * * * *